United States Patent [19]

Barton et al.

[11] Patent Number: 5,473,085

[45] Date of Patent: Dec. 5, 1995

[54] PRODUCTION OF (−)DODECAHYDRO-3A,6,6,9A-TETRAMETHYL-NAPHTHO[2,1-B] FURAN

[75] Inventors: Derek H. R. Barton; Dennis K. Taylor; Chi-Lam Tse, all of College Station, Tex.

[73] Assignee: Quest International B.V., Vlaardingen, Netherlands

[21] Appl. No.: 314,507

[22] Filed: Sep. 28, 1994

Related U.S. Application Data

[63] Continuation-in-part of Ser. No. 279,160, Jul. 22, 1994.
[51] Int. Cl.[6] ................................................. C07D 307/92
[52] U.S. Cl. ........................................................ 549/458
[58] Field of Search ............................................. 549/458

[56] References Cited

PUBLICATIONS

Barrero et. al., Tet., vol. 49(45) pp. 10405–10412 (1993).
Barton et. al. I, Tet. Letters, vol. 35(32) pp. 5801–5804 (1994).
Barton et. al. II, Tet. Letters, vol. 35(51) pp. 9505–9508 (Dec. 1994).

Primary Examiner—Bernard Dentz
Attorney, Agent, or Firm—Cushman Darby & Cushman

[57] ABSTRACT

Preparation of a methyl ketone intermediate useful in the synthesis of (−)-dodecahydro-3a,6,6, 9a-tetramethyl-naphtho(2,1-b) furan by subjecting (−)-sclareol to ozonolysis in the presence of iodine or iodine-containing compound. The intermediate can be converted to (−)-dodecahydro-3a,6,6, 9a-tetramethyl-naphtho(2,1-b) furan by Baeyer-Villiger oxidation followed by reduction of the resulting product in the presence of a Lewis acid.

12 Claims, No Drawings

PRODUCTION OF (−)DODECAHYDRO-3A,6,6,9A-TETRAMETHYL-NAPHTHO[2,1-B] FURAN

RELATED APPLICATION

The present application is a continuation-in-part of U.S. application Ser. No. 08/279,160, filed Jul. 22, 1994, the contents of which are incorporated herein by reference.

FIELD OF THE INVENTION

The present invention relates to the synthesis of the fragrance compound 1,2,3a,4,5,5a,6,7,8,9,9a,9b-dodecahydro- 3a,6,6,9a-tetramethylnaphtho-(2,1-b)-furan, which is also known as (−)-norlabdane oxide. The invention is particularly concerned with improvements in the preparation of an intermediate which is used in the synthesis of the indicated fragrance compound starting with sclareol.

BACKGROUND OF THE INVENTION

Norlabdane oxide may be structurally shown as follows:

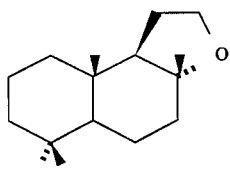
(1)

Compound (1) is presently one of the most commercially important perfume components for providing ambergris-type odors. Ambergris is a metabolic product of sperm whales which has been used in the past as a valuable constituent of fine fragrances.[1] Natural ambergris itself is no longer used for this purpose. However, there is a demand for perfume ingredients with ambergris-type odors. Compound (1) represents one of the preferred synthetic compounds with desirable ambergris-type odor and is commercially available under various names (notably as Amberlyn, Ambroxan, Ambrox or Amberoxide).[2]

Since the first reported synthesis of compound (1),[3] a number of synthesis procedures have been proposed. However, these are complex and laborious procedures which provide only a low yield of the desired product. Typically, these procedures include synthesis from sesqui- and diterpenoids.[4] More recently, it has been shown that naturally occurring (−)-sclareol[5,6] or communic acid[7,8] can be used as starting materials to prepare (1).

The reported procedures in going from the naturally occurring sclareol of structure (2):

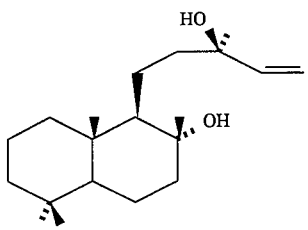
(2)

to the desired compound (1)[5,6], are, generally speaking, preferable to the communic acid pathways because the overall yields seem to be higher using (2), apparently due to a decrease in the number of steps required. In any case, all of the previously known methods using sclareol (2), as well as the current industrial process,[1] lead to the formation of the diol (3):

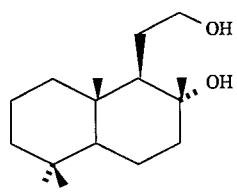
(3)

This must then be cyclized to give compound (1). This requires considerable care as the less desired, more thermodynamically stable iso-form of compound (1) may result[9,10]. This iso-form possesses inferior olfactive properties and serves to reduce the overall effectiveness of the synthesis process with respect to the production of compound (1).

In the above-mentioned application Ser. No. 08/279,160, we have described an improved process for preparing compound (1) starting with (−)-sclareol. The process involves a three-stage synthesis of compound (1) starting with sclareol (2) which avoids the cyclization step referred to above. The process comprises a reaction sequence wherein sclareol (2) is subjected to osmium tetroxide $OsO_4$, oxidation or catalyzed rearrangement to form methyl-ketone intermediates (4a) and (4b) after which intermediates 4(a) and 4(b) are converted by Baeyer-Villiger oxidation to give the acetates (5a) and (5b) which are both then converted e.g. by reduction in the presence of a Lewis acid to the desired compound (1). An advantage of the process is that epimeric mixtures of (4a) and (4b), hereinafter referred to for convenience as methyl ketone (4), may be used without separation since the products (5a) and (5b) obtained therefrom both give the desired compound (1) on reduction.

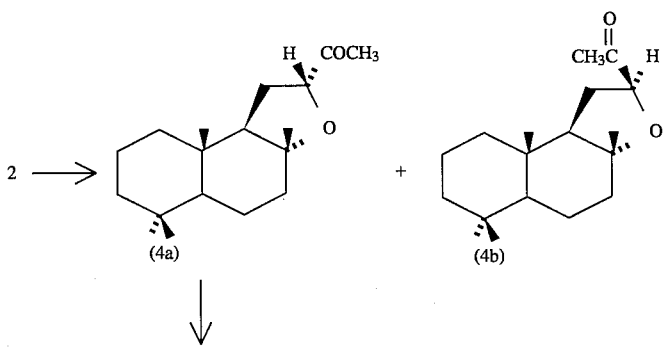

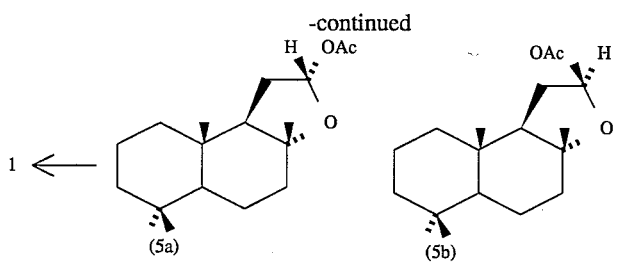

An important step in the process of Ser. No. 08/279,160 involves the osmium tetroxide/sodium periodate oxidation cleavage of (−)-sclareol followed by an osmium catalyzed rearrangement affording the methyl ketone (4) in excellent yield. As noted above, Baeyer-Villigar oxidation of the methyl ketone followed by reduction with a variety of reducing agents in the presence of a Lewis acid completes the synthesis of (−)-norlabdane oxide.

While the process of U.S. application Ser. No. 08/279,160 represents an important improvement over previously available procedures for making norlabdane oxide, it would be desirable, if possible, to avoid the use of osmium tetroxide which is expensive and toxic. Accordingly, the principal object of the present invention is to modify the process of U.S. Ser. No. 08/279,160 whereby the use of osmium tetroxide may be avoided while otherwise maintaining the advantages of the process described in Ser. No. 08/279,160. A more specific object of the invention is to provide an improved process for preparing the key methyl ketone intermediate (4) from sclareol whereby the ultimately desired flavoring product can be obtained more readily in outstanding yield.

SUMMARY OF THE INVENTION

Broadly defined, the invention involves preparation of the methyl ketone (4), i.e. the epimeric mixture of (4a) and (4b), predominantly as (4a), from (−)-sclareol by ozonolysis of sclareol in the presence of iodine or iodine-containing compounds, e.g. sodium periodate, $NaIO_4$. The resulting methyl ketone can then be converted to the desired product (1) in the manner described in the earlier application.

Other unique aspects of the invention will be evident from the more detailed description which follows.

DETAILED DESCRIPTION OF THE INVENTION

The ozonolysis of sclareol, according to the invention, may be carried out in several ways. One embodiment contemplates ozonolysing a reaction mixture comprising the sclareol and iodine or iodine-containing compound, in an inert solvent, preferably a lower alcohol or mixture thereof with water, to obtain the methyl ketone (4) in quantitative yield. In a modification, the sclareol, or iodine or iodine-containing compound, in solution may be preliminarily ozonolysed with further ozonolysis after the reactants are combined.

Reaction conditions can be varied. However, the ozonolysis, including any pre-ozonolysis, should preferably be carried out at acid pH, i.e. up to about 7. Ambient temperature (20°–25° C.) is advantageously used although temperatures above and below ambient, e.g. temperatures in the range of 10°–90° C. can be employed.

While free iodine may be effectively used, it is also possible to use iodine-containing compounds which apparently liberate iodine to facilitate the ozonolysis. Representative iodine-containing compounds include the alkali metal iodides, iodites, iodates and periodates, e.g. potassium iodide, sodium iodite, sodium iodate and sodium periodate. Alkyl iodides or iodites, e.g. methyl iodide or t-butylhypoiodite, may also be used. It is believed that the iodine-containing compound functions by liberating free iodine from the ozonolysis.

Any inert solvent may be used for present purposes. However, the lower alkanols, e.g. methyl alcohol, ethyl alcohol, n- or iso-propyl alcohol, n- or t-butyl alcohol, are particularly preferred. Mixtures of such alcohols with each other or with water may also be advantageously used.

The amount of iodine or iodine-containing compound relative to the sclareol can be widely varied. Usually, however, this will be in the range of about 0.25 to 4.0 molar equivalents of sclareol.

Reaction times can also be widely varied and will depend, at least to some extent, on other conditions, e.g. temperature and relative amounts of sclareol and iodine or iodine-containing compounds. Typically, reaction times will extend over the range of from 15 minutes up to 15 hours. The ozonolysis reaction should be continued long enough to convert all of the sclareol into methyl ketone (4) while minimizing the formation of other products.

It has been found that after ozonolysis of the sclareol a vinyl ether intermediate of structural formula (8) is formed:

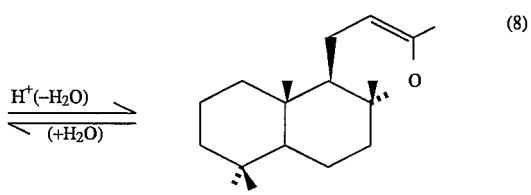

The invention is illustrated, but not limited, by the following examples:

Examples 1–17

Unless otherwise stated, all examples were carried out as follows:

$NaIO_4$ was added to a mixture of sclareol (0.2 g, 0.64 mmol) in methanol/water solution (25 mL, 4:1). The amount of $NaIO_4$ added was 3.0 equivalents (based on the amount of sclareol) for Examples 1–6; amounts as shown in Table 1 for Examples 7–9; 0.7 equivalents for Examples 10–16; and 1.0 equivalent of $NaIO_3$ in Example 17. The addition was carried out at 25° C.

Ozone was passed through the resulting mixture until all the sclareol was consumed (about 15 minutes as determined by TLC).

After 15 hours of additional stirring, the solvent was removed in vacuo and the residue dissolved in $CH_2Cl_2$ (80 mL), washed with 0.4M aqueous sodium thiosulphate (2×50 mL) and brine (2×50 mL). Desiccation with Mg $SO_4$ and removal of the solvent in vacuo afforded the products shown in Table 1. The product distributions were determined from $^1H$ and $^{13}C$ NMR analysis or by isolation using flash chromatography. The results obtained are given in Table 1 which also indicate in the "Conditions" column, any process variations which were used from those given above.

TABLE 1

| Example | Conditions | Products (%) | | | | | | |
|---|---|---|---|---|---|---|---|---|
| | | 4 | 5 | 6 | 7 | 8 | 9 | 10 |
| 1 | MeOH/$H_2O$ (4:1) at 0° C. | 46 | 14 | — | 17 | — | — | — |
| 2 | $^1$BuOH/$H_2O$ (4:1) at 25° C. | — | 26 | 19 | — | — | — | — |
| 3 | $^1$AmOH/$H_2O$ (4:1) at 0° C. | 7 | — | 42 | — | — | — | — |
| 4 | Temp. = 40° C. | 51 | 16 | — | 8 | — | — | — |
| 5 | Temp. = 25° C. | 51 | 23 | — | 7 | — | — | — |
| 6 | Temp. = −78° C. | — | 14 | — | 23 | 23 | — | — |
| 7 | $NaIO_4$ (1.3 equiv) | 48 | 12 | — | 9 | — | 2 | 9 |
| 8 | $NaIO_4$ (0.7 equiv) | 63 | 5 | — | — | — | 6 | 5 |
| 9 | $NaIO_4$ (0.2 equiv) | 38 | 4 | — | — | — | 4 | 26 |
| 10 | reaction time = 15 min | 25 | 8 | — | — | 25 | 11 | 22 |
| 11 | reaction time = 30 min | 63 | 5 | — | — | — | 6 | 5 |
| 12 | reaction time = 2 hr. | 54 | 15 | — | — | — | 12 | 6 |
| 13 | no $NaIO_4$ added | — | 16 | — | — | 23 | — | — |
| 14 | pH = 1.0 | 5 | 40 | — | 24 | — | — | — |
| 15 | pH = 2.95 | 62 | 7 | — | — | — | 9 | 11 |
| 16 | $NaIO_4$ ozonolysed first | 77 | 13 | — | 5 | — | — | 4 |
| 17 | $NaIO_3$ | 51 | — | — | — | 6 | 7 | — |

The pH was adjusted with phosphoric acid (Example 14) or sodium acetate (Example 15).

Product (4) represents the methyl ketone mixture (4a) and (4b) while products (5)–(10) are identified below. Products 11 and 12, referred to later, are also structurally identified below:

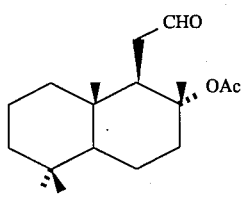

5

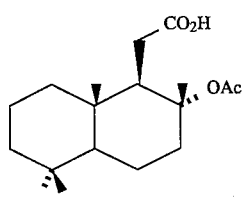

6

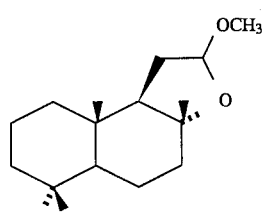

7

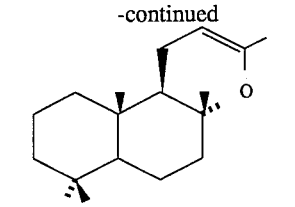

8

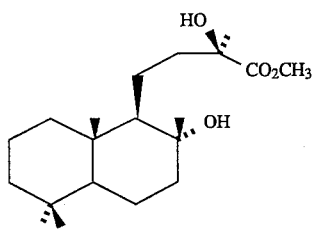

9

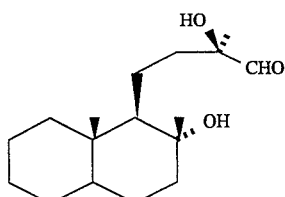

10

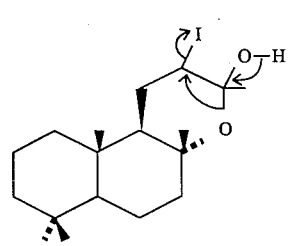

11

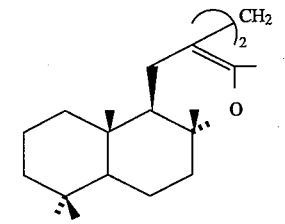

12

The identity of the above products is consistent with micro analysis results. Compounds (5), (6) and (8) had spectral and physical properties consistent with those reported in the literature.[11]

As shown, the results given in Table 1 indicate that under otherwise comparable circumstances, the best yield of the methyl ketone (4) was obtained when somewhat less than the equivalent of $NaIO_4$ (i.e. 0.7 equivalents) was used. Compare Examples 7–9. Use of greater amounts of $NaIO_4$ up to 3 equivalents did not increase the yield and, in some instances, tended to reduce, the yield.

Under shorter reaction times (see Examples 10–12), intermediates (8)–(10) were identified. The vinyl ether (8) was determined to be the key intermediate in these reactions by subjecting sclareol to ozonolysis without the addition of $NaIO_4$. See Example 13.

Only traces of the desired methyl ketone (4) were obtained below a pH of 2.95. See Example 14 where the amount of methyl ketone (4) was low compared to the substantial quantities of compounds (5) and (7) which were formed. However, excellent yields of the desired methyl ketone were obtained at a pH of about 3 (2.95). It appears that such yields can be realized when using any pH in the range of about 2.5 to about 7.5 for the ozonolysis in the presence of iodine, iodate or periodate or the equivalent.

As indicated, the formation of the methyl ketone (4) is considered to proceed via the vinyl ether (8). It is not completely clear how this conversion of (8) to (4) occurs. However, it is interesting to note that treatment of the vinyl ether (8) with $NaIO_4$ does not give the methyl ketone. On the other hand, ozonolysis of an aqueous methanolic solution of $NaIO_4$ yielded a white precipitate and it was surprisingly found that the treatment of the vinyl ether (8) with either this precipitate or the remaining filtrate quantitatively converted the vinyl ether (8) into the methyl ketone. This led to the finding that there is an advantage in subjecting the $NaIO_4$ to ozonolysis prior to addition of the sclareol. Example 16 illustrates this embodiment and shows that a substantial increase in the yield of the methyl ketone (4) was realized when the periodate was subjected to ozonolysis before the sclareol was mixed therewith, followed by further ozonolysis after the mixture is completed.

Example 17 demonstrates the use of $NaIO_3$ in lieu of $NaIO_4$ for the ozonolysis. As indicated, this alternative also gave a useful yield of the methyl ketone (4).

Without intending to be bound or limited to this explanation, it appears that the intermediate (8) is formed after the so-called "anomalous ozonolysis[12] of sclareol in a manner similar to that observed with other allylic alcohols.[13]

The following Examples 18–24 show further process variations within the invention. These examples illustrate ozonolysis of sclareol in the presence of iodine under a variety of conditions to obtain the methyl ketone (4) pursuant to the invention:

Examples 18–24

Each of these examples, unless otherwise stated, was carried out as follows:

To a mixture of sclareol (0.2 g, 0.64 mmol) in isopropanol, t-butanol or methanol (20 mL, water added as shown in Table 2), iodine (0.1 g, 0.38 mmol) was added at 25° C. Ozone was then passed through the mixture for 10–12 minutes after which the mixture was stirred for an additional 15 hours at ambient temperature. Work-up of the reaction product was the same as in Examples 1–17.

Isopropanol was used in Examples 20–31. Additionally, in Examples 21–23 and 28–31, the isopropanol/iodine mixtures were pre-ozonolysed for 10 minutes before the addition of water and sclareol. Ozonolysis was then continued for a further 5 minutes after which time the reaction mixture was stirred for an additional 15 hours at ambient temperature and worked up in the same way as in the other examples.

TABLE 2

Ozonolysis of (−)-Sclareol in the presence of iodine under a variety of conditions

| Examples | Conditions | Yield (4) (%) |
|---|---|---|
| 18 | MeOH | 62 |
| 19 | $^tBuOH$ | 23 |
| 20 | isopropanol | 65 |
| 21 | $I_2$ (1.0 equiv.) | 72 |
| 22 | $I_2$ (0.5 equiv.) | 71 |
| 23 | $I_2$ (0.2 equiv.) | 48 |
| 24 | 0.25 mL $H_2O$ added | 53 |

TABLE 2-continued

Ozonolysis of (−)-Sclareol in the presence of iodine under a variety of conditions

| Examples | Conditions | Yield (4) (%) |
|---|---|---|
| 25 | 0.5 mL $H_2O$ added | 69 |
| 26 | 1.0 mL $H_2O$ added | 60 |
| 27 | 10.0 mL $H_2O$ added | 34 |
| 28 | 0.25 mL $H_2O$ added | 85 |
| 29 | 0.5 mL $H_2O$ added | 86 |
| 30 | 1.0 mL $H_2O$ added | 84 |
| 31 | 2.0 mL $H_2O$ added | 64 |

Various modifications are evident from the results shown in Table 2. For example, Examples 18–20 show that methanol and isopropanol are useful solvents in providing effective yields of the desired methyl ketone on ozonolysis of sclareol. The yield using t-butanol, however, while useful, is not as good as that obtained with methanol and isopropanol.

Table 2 also shows (Examples 21–23, 38–31) that the yield of methyl ketone can be increased by ozonolysing the isopropanol/iodine solution (10 mins.) prior to addition of the (−)-sclareol with Example 22 showing that one-half the equivalent of iodine can be effectively used under such conditions.

The addition of a small amount of water to the alcohol was also found to increase the yield of methyl ketone (see Examples 24–27), particularly when combined with pre-ozonolysis of the alcohol/iodine solution (Examples 28–31). The results obtained with the addition of water suggest that HOI, rather than free-iodine, may function as intermediate reaction agent in the preparation of the methyl ketone (4).

More specifically, it is believed that the electrophilic iodine species HOI may be generated in the reaction medium and that this species may be responsible for the conversion of the vinyl ether (8) to the methyl-ketone (4) via intermediate (11). This appears to be substantiated by the fact that iodine is liberated during the reaction. The possible formation of HOI is also supported by the increased yields which are obtained when water is used with the alkanol solvent.

While the reaction conditions can be varied, as evident from the foregoing, the best results in the preparation of the methyl ketone (4) appear to be obtained when an isopropanol/iodine solution is initially ozonolysed prior to addition of the sclareol and a small but effective amount of water (e.g. about 5 to 30% or more, based on the weight of the sclareol).

While the foregoing Examples 18–31 illustrate the use of iodine for the ozonolysis, excellent results have also been obtained by replacing the iodine with, for example, potassium iodide. Thus, yields of the methyl ketone in the range of 80–83% have been obtained using potassium iodide in lieu of iodine, as the iodine providing component for the ozonolysis.

The product (12) has also been identified in the process when (−)-sclareol was subjected to ozonolysis in isopropanol. After 10 minutes, the solvent was removed and the residue recrystallized from pentane affording the dimer (12). The formation of (12) apparently comes from the reaction of the vinyl ether (8) and formaldehyde, a by-product of the ozonolysis reaction that has been identified previously.[11]

Examples 32–37 further illustrate various aspects of the invention:

Example 32

To prepare the desired norlabdane oxide, the methyl ketone (4), obtained as described in the preceding examples, may be converted by Baeyer-Villiger oxidation to give acetates which are then reduced in the presence of a Lewis acid to the desired product, all as described in the earlier U.S. application Ser. No. 08/279,160.

As indicated in Ser. No. 08/279,160, the methyl ketone (4) need not be separated into its individual components (4a) and (4b) for further reactions. Accordingly, to 1 g of the methyl ketone (4) in a 50 ml round bottomed flask, 1.2 g of 6% m-CPBA (Aldrich) and 0.65 g of NaOAc were added. 20 ml of distilled dioxane was then added and the mixture was stirred at room temperature for 1 day. A milky suspension resulted.

After stirring at room temperature for 1 day, the reaction mixture was poured into 50 ml of saturated aqueous sodium bicarbonate solution and diluted with 50 ml methylene chloride. After the extraction, the organic layer was separated, the aqueous layer was extracted with 3 more portions of 25 ml $CH_2Cl_2$, the organic layers were combined, dried and the solvent was evaporated. To purify the resulting compound (5a), flash Column chromatography was used; gradient elution with hexanes and ether. Compound (5a) eluted out at around 15% ether in hexanes. A maximum yield of 75% of compound (5a) was obtained.

To 0.07 g of $LiAlH_4$ in 10 ml of ether at 0° C., 0.85 ml dry distilled $BF_3.OEt_2$ was added. The mixture was stirred for 30 minutes, then it was cooled to −78° C. with dry ice/acetone. A solution of 0.5 g of compound (5a) was then added and the mixture was stirred at −78° C. for 30 minutes. The temperature was then raised slowly to room temperature.

The reaction was completed in about 3 hours and was followed by TLC.

After the reaction was completed, the reaction mixture was poured slowly into saturated aqueous sodium bicarbonate solution and 50 ml ether was added. After the extraction, the aqueous layer was extracted with 3 more portions of 25 ml ether, the organic layer was combined, dried and solvent was removed. The crude contained almost pure compound (1).

Compound (1) was purified by column chromatography to give a yield of 100% based on (5a).

While (5a) was separated in step 2 for conversion to (1), this was found not to be necessary since (5b) is likewise converted to compound (1) using step (3) to obtain an even higher overall yield.

The following additional examples are provided to further illustrate aspects of the invention:

Example 33

This example illustrates the ozonolysis of (−)-sclareol with ozonolysed sodium periodate to obtain the methyl ketone (4) as an epimeric mixture of (4a) and (4b).

0.67 g (3.1 mmol) of sodium periodate was dissolved in 20 ml of methanol and 5 ml water and the mixture was ozonolysed for 30 minutes. Ozonolysis was stopped and the solution was bubbled with oxygen for 5 minutes after which 0.2 g (0.64 mmol) of sclareol was added and the solution was again ozonolysed. The reaction was followed by TLC and the reaction completed in 5 minutes. The solution was stirred at room temperature for 15 hours. The solvent was then removed in vaccuo and the residue was dissolved in 80 ml of methylene chloride. The organic layer was washed with two 50 ml portions of 0.4M aqueous sodium thiosulphate solution and two 50 ml portions of saturated sodium bicarbonate solution. The organic layer was dried and the solvent was removed. On column chromatography, 77% of (4) was isolated (4a:4b 4:1).

The ozonolysis in this example and in all the preceding examples was conducted as follows:

Ozone was generated by a Welsbach Model T-408 ozonator using 99.9% oxygen without further purification. The voltage was set at 100 V, pressure at 5 lb/in$^2$ and the flow rate was 0.02 ml$_3$/min. Ozone was introduced to the reaction mixture in a round bottom flask by a narrow pipet. The flow rate of ozone in the effluent stream of the ozonised gas from the ozonator was measured by a standard aqueous potassium iodide solution at determined time intervals and the iodine produced was back titrated by sodium thiosulphate solution. It was found that the flow rate of ozone was 4 mmol/min. This procedure was followed for all ozonolyses described herein unless otherwise specified.

Example 34

This example illustrates the ozonolysis of (−)-sclareol to prepare the methyl ketone (4) using pre-ozonolysed iodine:

0,096 (0.38 mmol) of iodine was dissolved in 20 ml of isopropanol. The solution was ozonolysed as in Example 33 at room temperature (25° C.) for 10 minutes, then bubbled by oxygen for 5 minutes after which 0.2 ml of distilled water and 0.2 g (0.64 mmol) of sclareol were added. The solution was stirred at room temperature for 15 hours and the reaction was then worked up as in Example 33 to give 85% of the methyl ketone as an epimeric mixture of 4a:4b in about a 4:1 ratio.

Example 35

This example illustrate the invention by reaction of ozonolysed sclareol with potassium iodide:

0.2 g (0.64 mmol) of sclareol was dissolved in 20 ml of isopropanol. The solution was ozonolysed for 5 minutes after which a suspension of 0.4 g (2.5 mmol) of potassium iodide in glacial acetic acid was added. The solution immediately turned from colorless to dark brown. The solution was stirred at room temperature for 15 hours and worked up as in Example 33. A yield of 82% of the methyl ketone (4) was obtained with a 10:1 ratio of (4a) to (4b).

Features of the invention are further illustrated by the following examples which illustrate the preparation of the methyl ketone (4) in epimeric mixture from vinyl ether (8), the latter being initially prepared by the ozonolysis of (−)-sclareol as described earlier herein.

Example 36

This example illustrates the preparation of the methyl ketone (4) using iodine:

To 0.1 g of (0.38 mmol) of the vinyl ether (8) in 20 ml. of t-butanol, 0.19 g (0.39 mmol) of iodine was added (pH=1). The solution was stirred at room temperature for 15 hours. The reaction mixture was then poured into 50 ml of 0.4M sodium thiosulfate solution. The aqueous layer was extracted with four 20 ml portions of methylene chloride. The organic layer was washed with two 50 ml portions of saturated sodium bicarbonate solution and two 50 ml portions of brine. The organic layer was then dried over anhydrous magnesium sulfate and the solvent was evaporated. The residue was almost pure methyl ketone (4). The residue was chromatographed and 0.1 g of the methyl ketone with a 4:1 ratio of ra:(4b) was isolated.

Quantitative yields of the methyl ketone were obtained when the t-butanol was replaced by isopropanol and/or methanol.

Example 37

This example illustrates the preparation of the methyl ketone epimeric mixture from vinyl ether (8) using t-butyl-hypoiodite as the iodine-containing compound. The example also illustrates the importance of using an acid pH.
a. basic pH To 0.19 g (0.39 mmol) of iodine in 20 ml t-butanol, 0.06 g (0.53 mmol) of potassium t-butoxide was added. The resulting solution was stirred for 15 minutes. The pH of the solution was 11.

0.1 g (0.38 mmol) of the vinyl ether (8) was added to the solution and the solution was then stirred at room temperature for 15 hours. No reaction was observed and the starting material was recovered.
b. acidic pH To 0.19 g (0.39 mmol) of iodine in 20 ml t-butanol, 0.06 g (0.53 mmol) of potassium t-butoxide was added. The solution was stirred for 15 minutes and it was then acidified by addition of 30% phosphoric acid until a pH of 0.88 was obtained. Thereafter, 0.1 g (0.38 mmol) of the vinyl ether was added and the solution was stirred at room temperature for 15 hours. The reaction mixture was then poured into 50 ml of 0.4M sodium thiosulfate solution and the aqueous layer was extracted with four 20 ml portions of methylene chloride. The organic layer was washed with two 50 ml portions of saturated sodium bicarbonate solution and two 50 ml portions of brine. The organic layer was dried over anhydrous magnesium sulfate and the solvent was evaporated. The residue was chromatographed and 0.105 g of methyl ketone, with a 4:1 ratio of (4a):(4b), was isolated.

As will be evident from the foregoing, the invention may be practiced in a variety of ways. Thus, the sclareol and/or iodine or iodine-containing compound may be separately preozonolysed before further ozonolysation to obtain the desired methyl ketone. When the sclareol is pre-ozonolysed, the resulting vinyl ether intermediate (8) may or may not be isolated. Preferably, however, the procedure is carried out without isolating the intermediate.

The following publications are referred to earlier herein:

References

1. Sell, C., *Chemistry and Industry*, 20:516–520, 1990
2. Ohloff, G., *Fragrance Chemistry. The Science of the Sense of Smell*, Theimer, E. T.; Academic Press, New York, 1982, pp. 535–573
3. Stoll, M., Hinder, M., *Helv. Chim. Acta*, 33:1251–1261, 1950; Hinder, M., Stall, M., *ibid* 1308–1312
4. Gonzalez-Sierra, M., Ruvida, E. A., Lopez, J. T., Cortes, M. J., *Hetercycles*, 26:2801–2804, 1987; Schenk, H. R., Gutman, H., Jeger, O., Ruzicka, L., *Helv Chim. Acta*, 37:543–546, 1954; Cambie, R.C., Joblin, K. N., Preston, A. F., *Aust. J. Chem.*, 24:583–591, 1971; De-Pascual, T. J., Urones, J. G., Montana, P. A., Basabe, P., *Tetrahedron Lett.*, 26:5717– 5720, 1985; Koyama, H., Kaka, Y., Ohno, M., *Tetrahedron Lett.*, 28:2863–2866, 1987; Nishi, Y., Ishihara, H., *J. Jpn. Oil Chem. Soc.*, 38:276–279, 1989
5. Martres, P., Perfetti, P., Zahra, J. P., Waegell, B., Giraudi, E., Petrzilka, M., *Tetrahedron Lett.*, 34:629–632, 1993; Martres, P., Perfetti, P., Zahra, J. P., Waegell, B., *Tetrahedron Lett.*, 32:765– 766, 1991; Coste-Maniere, I. C., Zahra, J. P., Waegell, B., *Tetrahedron Lett.*, 29:1017–1020, 1988; Martres, P., Perfetti, P., Zahra, J. P., Waegell, B., *Tetrahedron Lett.*, 35:97–98, 1994
6. Barrero, A. F., Enrique, J. E., Manzaneda, A., Altarejos, J., Salido, S., Ramos, J. M., *Tetrahedron*, 49:10405–10412, 1993
7. Barrero, A. F., Altarejos, J., Enrique, J. E., Manzaneda, A., Ramos, J. M., Salido, S., *Tetrahedron*, 49:6251–6262, 1993
8. Barrero, A. F., Altarejos, J., Enrique, J. E., Manzaneda, A., Ramos, J. M., Salido, S., *Tetrahedron*, 49:9525–9534, 1993
9. Buchi, G.; Wuest, H.; *Helv. Chim. Acta* 1989, 72, 996–999.
10. Decorzant, R.; Vial, C.; Naf, F.; *Tetrahedron* 1987, 43, 1871–1879.
11. Vlad et al, U.S.S.R. SU 1,409,631 (Cl. CO7D307/92), 15 Jul. 1988, Appl. 4,001,468, 03 Jan. 1986, from *Otkrytiya. Izobret.*, 1988, 26, 94
12. Bailey, P. S., "Ozonolysis in Organic Chemistry", New York: Academic Press, 1978, Chapter 9, pp. 147–180
13. Mosettig, E., Berlinger, U., Dolder, F., Lichti, H., Quitt, P., Waters, J. A., *J. Org. Chem.*, 85:2305–2309 (1963); Young, W. G., McKinnis, A. C., Webb, I. D., Roberts, J. D., *J. Org. Chem.*, 68:293–296 (1946); Vlad, P., Soucek, M., *Collection Czechoslov. Chem. Commun.*, 27:1726–1729 (1962)

Various modifications may be in the invention as described herein. Hence, the scope of the invention is defined in the following claims wherein:

We claim:

1. In a process for preparing (−)-dodecahydro-3a, 6,6,9a-tetramethylnaphtho(2,1-b) furan of the formula (1):

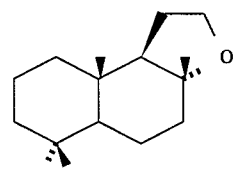

(1)

which comprises:

(i) converting sclareol of the formula (2)

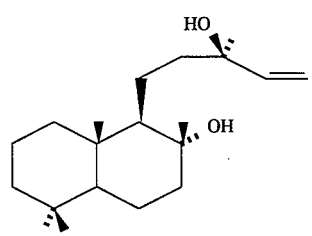

(2)

to methyl ketones of the formulae:

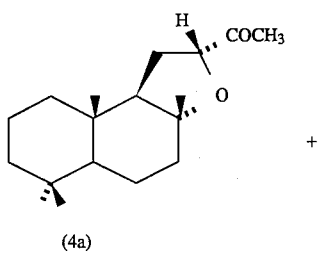

(4a)

+

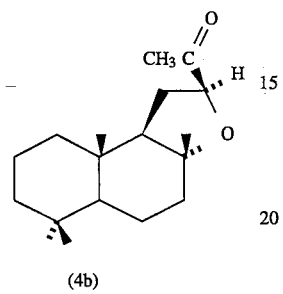

(4b)

(ii) converting said ketone (4a) or mixture thereof with (4b) to, respectively, an acetate of the formula (5a) or mixture of acetates (5a) and (5b):

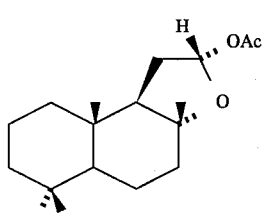

(5a)

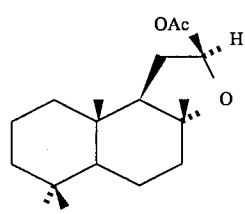

(5b)

and (iii) converting said acetate (5a) or acetate mixture (5a) and (5b) to said compound (1), the improvement which comprises carrying out step (i) by ozonolysis of the sclareol in the presence of iodine or an iodine-liberating compound.

2. The process of claim 1 wherein the ozonolysis of step (i) is carried out in the presence of iodine in alcohol solution.

3. The process of claim 1 wherein the ozonolysis of step (i) is carried out in the presence of an alkali metal iodate, iodite, iodide or periodate in alcohol solution.

4. The process of claim 2 wherein the alcohol is a lower alcohol or mixture thereof with water.

5. The process of claim 2 wherein the ozonolysis is carried out at a pH of up to about 7.

6. The process of claim 2 wherein the sclareol is initially subjected to ozonolysis in the absence of iodine compound and ozonolysis is thereafter continued in the presence of iodine.

7. The process of claim 2 wherein an iodine solution is ozonolysed after which sclareol is added to the solution and the ozonolysis is continued to form the methyl ketone.

8. The process of claim 1 wherein step (ii) comprises oxidation of (4a).

9. The process of claim 1 wherein the oxidation of 4(a) and 4(b) is a Baeyer-Villiger oxidation.

10. The process of claim 1 wherein step (iii) is carried out by deacetylation of compound (5a) and 5(b).

11. A process for preparing a methyl ketone of formula 4(a) or 4(b)

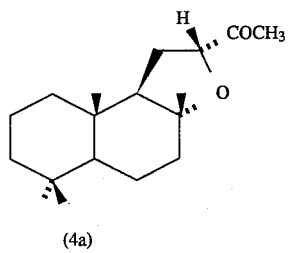

(4a)

+

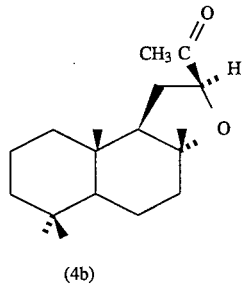

(4b)

which comprises subjecting sclareol to ozonolysis in the presence of iodine or an iodine-containing compound.

12. The process of claim 11 wherein a vinyl ether is first formed by subjecting sclareol to ozonolysis and the vinyl ether is thereafter converted to the methyl ketone in the presence of iodine or positive iodine-containing compound.

* * * * *